United States Patent [19]
Lokken

[11] 4,424,036
[45] Jan. 3, 1984

[54] ANTI-SPLASH CUP FOR DENTAL PROPHYLAXIS

[76] Inventor: Oddvin Lokken, 131 Forest Ave., Rye, N.Y. 10580

[21] Appl. No.: 359,223

[22] Filed: Mar. 18, 1982

[51] Int. Cl.³ .............................................. A61C 1/16
[52] U.S. Cl. ................................................... 433/116
[58] Field of Search .................... 433/116, 114, 87

[56] References Cited
U.S. PATENT DOCUMENTS
2,731,722  1/1956  Wilen .................................. 433/116

FOREIGN PATENT DOCUMENTS
2024656  11/1971  Fed. Rep. of Germany ...... 433/116

Primary Examiner—Robert Peshock
Attorney, Agent, or Firm—Jacobs & Jacobs

[57] ABSTRACT

An anti-splash device for attachment to a dental tool having apparatus for delivering water from the head thereof during use, comprising an elongated, hollow member and a member for securing said hollow member to the head of said dental tool, said hollow member being adapted to surround and be spaced apart from said water delivery apparatus.

15 Claims, 9 Drawing Figures

ANTI-SPLASH CUP FOR DENTAL PROPHYLAXIS

The present invention relates to an accessory for a dental tool and more particularly to a device for confining to the patient's mouth the splashing of water and debris normally encountered during dental prophylaxis.

It is well known that there is considerable splashing of water, dental paste and debris during dental prophylaxis due to the centrifugal forces exerted by the rapidly rotating rubber "prophy-cup". Despite care exercised by the dentist or dental hygienist, the splashing encountered during the dental prophylaxis often sprays the gown, face, hair and glasses of the dentist or hygienist, and sometimes the patient's garments as well. In addition, the dentist or hygienist may be contaminated by bacterial or other hazardous debris which the patient may harbor in his mouth, and there have been occasions where the dentist or hygienist, his assistant and sometimes even the patients themselves have suffered an eye injury from this debris.

In recognition of this problem, the patient and the dentist and/or hygienist must be extensively draped to prevent soiling of their clothing, and the dentist's office and equipment, such as operating lights and walls, must be inspected and cleaned, as necessary, after the dental prophylaxis has been completed.

There is thus a need in the art to avoid these problems which arise from the conventional dental prophylaxis equipment.

The present invention now provides a device for confining the splashing normally encountered during dental prophylaxis to the mouth of the patient. This is accomplished in accordance with the invention by the provision of an anti-splash device which comprises an inverted cup having a neck portion and an integral, flexible, open skirt portion extending outwardly and downwardly from said neck portion and defining an open bell-shaped chamber within said skirt portion, said neck portion having a central bore therethrough extending into said chamber, at least that part of said skirt portion adjacent said neck portion being transparent.

The present invention is illustrated in terms of a preferred embodiment in the accompanying drawing in which.

Figure 1:
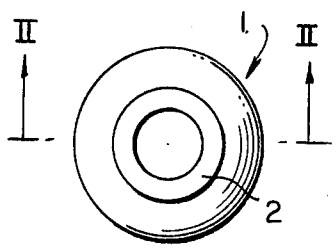
FIG. 1 is a top view of the anti-splash cup of the invention.
Figure 3:
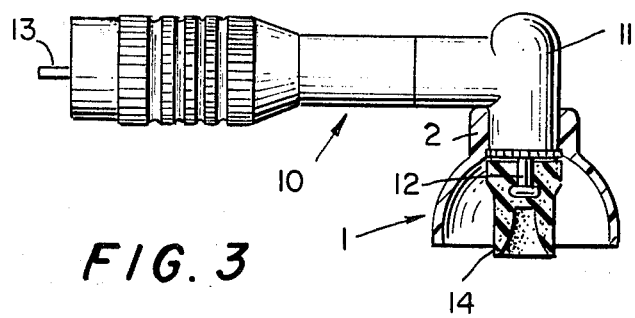
FIG. 3 is an elevational view, partly in section, of a dental tool carrying a conventional prophy-cup and an anti-splash cup of the invention.
Figure 2:
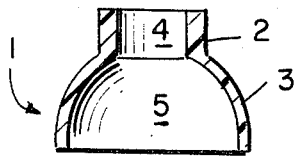
FIG. 2 is an elevational view in section along line II—II of FIG. 1.

Referring to drawing, FIGS. 1 and 2 show the anti-splash cup 1 of the invention, which is made of a transparent, flexible material, such as rubber or plastic. The cup 1 has an upper neck portion 2 and an integral depending skirt portion 3. Within the neck portion 2 is an aperture or bore 4. As best seen in FIGS. 2 and 3, the skirt portion 3 encloses a large, open bell-shaped chamber 5.

Referring to FIG. 3, dental tool 10 is a conventional dental tool that is normally attached to a dental handpiece (not shown) which supplies power to dental tool 10. The dental tool 10 has at one end a head 11 from which extends a rotating shaft 12. At the other end of the dental tool 10 is a drive shaft 13, which interconnects with a power source (not shown) so that the rotating shaft 12 may be selectively activated. Attached to the rotating shaft 12 is a conventional prophy-cup 14, usually made of rubber, which is supplied with prophy paste in a conventional manner for use in dental prophylaxis.

The anti-splash cup 1 is attached to the dental tool 10 by sliding the neck portion 2 over head 11. Head 11 is retained in the bore 4 of anti-splash cup 1 by frictional engagement. In this manner, there is no need to make any modifications in the conventional dental tool 10 for the purpose of attaching anti-splash cup 1 to the tool 10. If desired, however, the neck portion 2 may carry means (not shown) that cooperate with the head 11 for securing the cup 1 to the tool 10, such as a ring or groove on the neck 2 and a cooperating groove or ring on the head 11.

The skirt portion of the anti-splash cup 1 opens or spreads outwardly from the neck portion 2. When the dental tool 10 carries the anti-splash cup 1, the flaring skirt 3 will prevent the water and debris normally encountered during dental prophylaxis from flying out of the patient's mouth. Thus, the internal surface of the flaring skirt 3 will catch this debris and the debris will thus be confined to the oral cavity.

Figure 4:
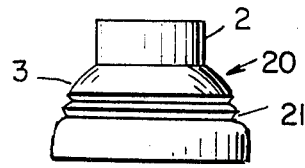
FIG. 4 shows an elevational view of another embodiment of the invention.

FIG. 4 shows an alternative splash cup 20 which has a neck portion 2, a flaring skirt 3 and a pleated section 21 to provide additional flexibility to the anti-splash cup 20. The added flexibility of the cup 20 due to the pleated section 21 is particularly useful when cleaning the surfaces of the teeth near the cheek and/or on the rearmost teeth where there is less room to maneuver.

Figure 5:
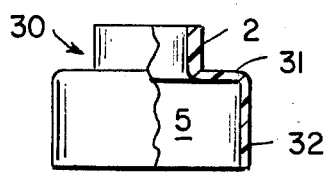
FIG. 5 is an elevational view, partly in section, showing a further embodiment of the invention.

FIG. 5 shows a further alternative splash cup 30 which has a neck portion 2 and a lower bell-shaped chamber 5. In cup 30, the skirt has an upper flat portion 31 and a lower cylindrical portion 32. In this embodiment, the flat surface of portion 31 will have less optical distortion than the curved surface of the skirt 3 and will provide enhanced visibility.

Figure 6:
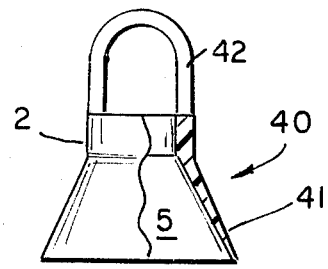
FIG. 6 is an elevational view, partly in section, of another embodiment of the invention.

FIG. 6 shows another alternative splash cup 40, which has a frustoconical skirt 41 rather than the convex skirt 3. Splash cup 40 has an integral strap 42 in the form of an inverted U extending between diametrically opposed points at the top of neck portion 4. This thin strap or band is used to provide additional means for securing the splash cup to the head 11. Thus, after the cup 40 is slid over the bottom of head 11, the strap 42 is slipped over the top of head 11 so that the strap 42 grips the head 11. Of course, any of the other splash cups can be provided with such a strap or band.

Figure 7:
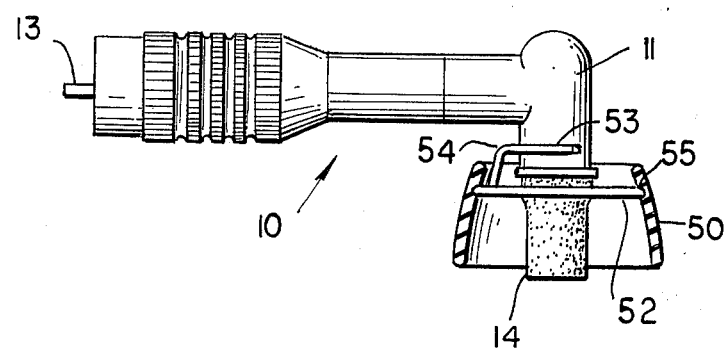
FIG. 7 is a view similar to FIG. 3, showing an alternative embodiment of the invention.
Figure 8:
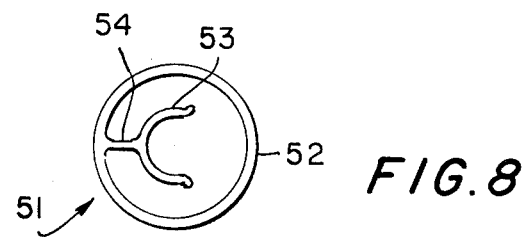
FIG. 8 is a top view of the clip used in the embodiment of FIG. 7.

FIG. 7 shows another embodiment of the invention, in which the anti-splash cup 50 is in the form of an open cylinder. While cup 50 is preferably made of transparent plastic, it may also be opaque. Cup 50 is secured to the free end of head 11 by means of metal or plastic clip 51. Thus, clip 51 has a lower ring portion 52 and an upper springclip 53 connected via intermediate member 54. A groove 55 in the inner surface of cup 50 matingly receives ring portion 52. If desired, clip 51 and cup 50 may be molded from plastic as a single unit. Cup 50 will serve to confine the water and debris to the patient's mouth during dental prophylaxis, and, additionally, will provide more visibility through the open top of cup 50.

Figure 9:
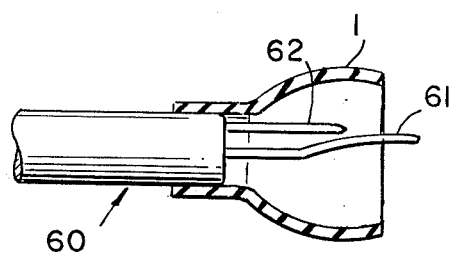
FIG. 9 is a partial elevational viewing showing the anti-splash cup mounted on an ultrasonic prophy unit.

FIG. 9 shows splash cup 1 attached to the head of an ultrasonic prophy unit, such as a "Cavitron" unit. The ultrasonic unit 60 has a vibrating ultrasound tip 61 and a water tube 62. Cup 1 will thus act to prevent water from splashing out of the patient's mouth during use of ultrasonic 60 in the same way as when it is used on dental tool 10.

It is understood that cup 50 need not be in the form of the open cylinder shown, but rather can be flaring as skirt 3 or frustroconical as skirt 41.

If desired, clip 51 (FIG. 7) can be permanently affixed to the free end of head 11, for example, by means of a suitable adhesive. This can be done at the time of manufacture of the dental tool 10 or thereafter by the purchaser of dental tool 10. With clip 51 attached to head 11, the user will replace only the cup 50 and not replace the entire unit 50,51. Replacement of a cup 50 is accomplished by disengaging ring portion 52 from groove 55 to allow removal of the cup, and the new cup is replaced by snapping ring portion 52 into groove 55 of the new cup.

What is claimed:

1. An anti-splash device for attachment to a dental prophylaxis tool having a dental prophylaxis member and means for delivering water from the head thereof during use, comprising an elongated, hollow tubular member and means for securing said hollow tubular member to the head of said dental tool in such a manner that the entire extent of said hollow tubular member is spaced apart from said head and is spaced apart from and surrounds said water delivery means, whereby the dental prophylaxis treatment may be observed through the space between said head and the top of said hollow tubular member.

2. The device according to claim 1, wherein said elongated, hollow member is generally cylindrical.

3. The device according to claim 1, wherein said elongated, hollow member flares outwardly from the longitudinal axis thereof.

4. The device according to claim 3, wherein said elongated, hollow member is frustoconical.

5. The device according to claim 1, wherein said securing means is a clip means carried by one end of said elongated, hollow member.

6. The device according to claim 1, wherein said elongated hollow member is integral with said securing means.

7. An antisplash device for attachment to a dental prophylaxis tool having a dental prophylaxis member and means for delivering water from the head thereof during use, comprising an elongated, hollow inverted cup having a neck portion and an integral, flexible, open skirt portion extending outwardly and downwardly from said neck portion and defining an open bell-shaped chamber spaced apart from said water delivery means within said skirt portion, said neck portion having a central bore therethrough extending into said chamber and being adapted to fit onto said head of said dental tool, at least that part of said skirt portion adjacent said neck portion being transparent to enable the dental prophylaxis treatment to be viewed.

8. The device according to claim 7, wherein said entire skirt portion is transparent.

9. The device according to claim 7, wherein said skirt portion is convex.

10. The device according to claim 7, wherein said skirt portion includes a flat annular part having an inner and an outer perimeter, said annular part being integral with said neck portion at said inner perimeter, and a curved part depending from said outer perimeter.

11. The device according to claim 7, wherein said skirt has at least one circumferentially pleat therein.

12. The device according to claim 7, wherein said skirt is frustoconical.

13. The device according to claim 7, wherein said skirt is made of plastic.

14. The device according to claim 7, wherein said skirt is made of rubber.

15. The device according to claim 7, including strap means in the form of an inverted U extending outwardly and upwardly from said neck portion for gripping said dental tool.

* * * * *